United States Patent
Breazeale

(10) Patent No.: US 9,554,939 B1
(45) Date of Patent: Jan. 31, 2017

(54) MAGNETIC RETINAL PATCH

(71) Applicant: Richard Breazeale, Signal Mountain, TN (US)

(72) Inventor: Richard Breazeale, Signal Mountain, TN (US)

(*) Notice: Subject to any disclaimer, the term of this patent is extended or adjusted under 35 U.S.C. 154(b) by 158 days.

(21) Appl. No.: 14/092,594

(22) Filed: Nov. 27, 2013

(51) Int. Cl.
*A61B 17/08* (2006.01)
*A61F 9/007* (2006.01)

(52) U.S. Cl.
CPC .................. *A61F 9/00727* (2013.01)

(58) Field of Classification Search
CPC ............... A61F 2/0063; A61F 9/00727; A61F 2210/009; A61F 9/00; A61F 9/0008; A61B 17/52; A61B 2017/00876
See application file for complete search history.

(56) References Cited

U.S. PATENT DOCUMENTS

| | | |
|---|---|---|
| 6,292,678 B1 | 9/2001 | Hall et al. |
| 6,542,766 B2 | 4/2003 | Hall et al. |
| 6,702,804 B1 | 3/2004 | Ritter et al. |
| 2005/0203333 A1 | 9/2005 | Dailey et al. |
| 2008/0051823 A1* | 2/2008 | Makower ........... A61B 17/1285 606/192 |
| 2010/0211184 A1* | 8/2010 | Rousseau et al. ......... 623/23.76 |
| 2011/0060320 A1* | 3/2011 | Aharon-Attar ................... 606/4 |
| 2011/0184440 A1 | 7/2011 | Saldinger |
| 2013/0178933 A1* | 7/2013 | Serrano Olmedo ...... A61F 2/14 623/4.1 |
| 2013/0231520 A1 | 9/2013 | Cherian et al. |

FOREIGN PATENT DOCUMENTS

ES          2024242          2/1992

* cited by examiner

*Primary Examiner* — Melanie Tyson
(74) *Attorney, Agent, or Firm* — Matthew M. Googe; Robinson IP Law, PLLC

(57) ABSTRACT

A retinal treatment apparatus for treatment of a detached retina of an eye is provided. The treatment apparatus includes a removable elastomeric patch formed of a biocompatible material containing ferromagnetic particles encapsulated within the elastomeric patch and a permanent rare-earth magnet secured adjacent an exterior surface of the eye. The removable elastomeric patch is inserted into the eye and positioned adjacent the detached retina, and wherein the permanent rare-earth magnet is secured to the exterior surface of the eye substantially adjacent to the removable elastomeric patch to maintain the elastomeric patch against the retina, thereby maintaining the retina against an underlying support tissue of the retina.

14 Claims, 8 Drawing Sheets

MAGNETIC RETINAL PATCH

FIELD

This disclosure relates to the field of ocular devices. More particularly, this disclosure relates to a magnetic ocular retinal patch for repairing a detached retina.

BACKGROUND

Retinal detachments occur when the retina peels away from its underlying support tissue, thereby allowing subretinal fluid to enter between the retina and underlying support tissue. Retinal detachments may occur as a result of a localized hole or tear in the retina and may rapidly spread potentially resulting in detachment of the entire retina if left untreated, ultimately resulting in severe vision impairment or blindness.

Retinal detachment may occur in three ways: (1) rhegmatogenous retinal detachment; (2) fractional retinal detachment; and (3) exudative retinal detachment. Rhegmatogenous retinal detachment occurs when a hole or break forms in the retina, allowing the vitreous humor to flow between the retina and underlying support tissue and thereby cause the retina to detach. Tractional retinal detachment occurs when scar tissue causes the retina to detach from the underlying support tissue. Finally, exudative retinal detachment occurs when fluid seeps out of blood vessels beneath the retina into a space between the retina and underlying support tissue, thereby causing the retina to detach.

A number of treatment options currently exist but each of them include varying drawbacks. One method of treatment is scleral buckle surgery in which one or more bands may be attached to the sclera of the eye. The one or more bands may push the wall of the eye inward towards the retinal hole or tear and remain in place until the retina re-attaches to the underlying support tissue. However, scleral buckle surgery often results in myopic shift and other complications.

Another traditional form of treatment is through pneumatic retinopexy, wherein a gas bubble is injected into the eye followed by laser or freezing treatment to the hole or tear in the retina. The patient is then positioned such that the gas bubble migrates to a position adjacent to the site of the hole or tear in the retina until the retina has healed. However, pneumatic retinopexy requires that the patient maintain their head in a designated position to maintain the bubble against the hole or tear in the retina, and further may be impractical when the hole or tear occurs in certain portions of the eye.

Recently, experiments have been conducted wherein a retinal detachment is treated with a ferrofluild. Specifically, the ferrofluid is injected into the eye and a magnetic source is placed adjacent to the site of detachment to attract the ferrofluid and thereby pull the retina against the underlying support tissue. However, this method of treatment has several drawbacks including displacement of the ferrofluid during treatment. Additionally, the ferrofluid may enter the sub-retinal space between the detached retina and underlying support tissue and prevent re-attachment of the retina. Finally, removal of the ferrofluid may be difficult because the individual magnetic particles may be dispersed within the eye or may drift under the retina between the retina and underlying support tissue. If magnetic particles remain in the eye, a patient may experience pain or other medical issues such as, for example, complications if the patient later undergoes a magnetic resonance imaging (MRI) procedure.

What is needed, therefore, is a simple method and apparatus for treating a retinal detachment that minimizes side effects and improves recovery results of the patient.

SUMMARY

The above and other needs are met by a magnetic retinal treatment apparatus for treatment of a detached retina of an eye. In a first aspect, the magnetic retinal treatment apparatus includes a removable elastomeric patch formed of a biocompatible material containing ferromagnetic particles encapsulated within the elastomeric patch and a permanent rare-earth magnet secured adjacent to the exterior surface of the eye. The removable elastomeric patch is inserted into the eye and positioned adjacent to the detached retina covering the retinal defect, and he permanent rare-earth magnet is secured to the exterior surface of the eye substantially adjacent to the removable elastomeric patch to maintain the elastomeric patch against the retina, thereby maintaining the retina against an underlying support tissue of the retina.

In one embodiment, the removable elastomeric patch is formed from a silicone elastomer. In another embodiment, the silicone elastomer is formed from commercially available Silastic® available from Dow Corning Corporation. In yet another embodiment, the ferromagnetic particles are formed from iron filings.

In one embodiment, the removable elastomeric patch has a thickness of from about 0.5 mm to about 2 mm. In another embodiment, the removable elastomeric patch has a total surface area of from about 5 mm$^2$ to about 800 mm$^2$.

In one embodiment, the ferromagnetic particles are substantially concentrated in one or more areas of the removable elastomeric patch along an area of the retina where a greater force is desired to be applied by the patch. In another embodiment, the ferromagnetic particles are substantially evenly distributed throughout the removable elastomeric patch.

In one embodiment, the permanent rare-earth magnet is secured to the exterior surface of the eye with an adhesive. In another embodiment, the retinal treatment apparatus further comprises a band positioned on or around the exterior of the eye for temporarily securing the permanent rare-earth magnet adjacent the exterior surface of the eye.

In yet another embodiment, the patch is substantially transparent.

In a second aspect, a method of repairing a detached retina of an eye is provided. The method of repairing a detached retina includes removing sub-retinal fluid from between the retina and an underlying support tissue of the eye; inserting a removable elastomeric patch into an interior of the eye, the removable elastomeric patch containing a plurality of ferromagnetic particles embedded within the elastomeric patch; positioning the removable elastomeric patch adjacent to the detached retina; positioning a permanent magnetic source adjacent to an exterior surface of the eye substantially aligned with the detached retina; and pulling the removable elastomeric patch against the detached retina with the magnet such that the detached retina is substantially maintained against the underlying support tissue by the removable elastomeric patch.

In one embodiment, the elastomeric patch is rolled prior to inserting the elastomeric patch into the interior of the eye. In another embodiment, the method further includes injecting a fluid into the interior of the eye after pulling the removable elastomeric patch against the detached retina wherein the removable elastomeric patch prevents fluid from passing through a hole or tear in the retina into a space between the retina and the underlying support tissue. In yet another embodiment, the method further comprises removing the elastomeric patch with a magnet retrieval tool.

In one embodiment, the method further comprises treating the retina with a concentrated energy beam (e.g., a laser) through the elastomeric patch.

In a third aspect, a method of forming a removable elastomeric patch for repairing a detached retina is provided. The method of forming a removable elastomeric patch for repairing a detached retina includes forming a continuous sheet of elastomeric material, the elastomeric material comprising a plurality of ferromagnetic particles embedded within the elastomeric material; forming a patch from the elastomeric material, the patch dimensioned to cover a desired area of the detached retina; and inserting the patch of elastomeric material into an interior of an eye adjacent the detached retina.

In one embodiment, the continuous sheet of elastomeric material is formed of a silicone elastomer. In another embodiment, the continuous sheet of elastomeric material is formed from commercially available Silastic®.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

DETAILED DESCRIPTION

Various terms used herein are intended to have particular meanings. Some of these terms are defined below for the purpose of clarity. The definitions given below are meant to cover all forms of the words being defined (e.g., singular, plural, present tense, past tense). If the definition of any term below diverges from the commonly understood and/or dictionary definition of such term, the definitions below control.

Figure 1:
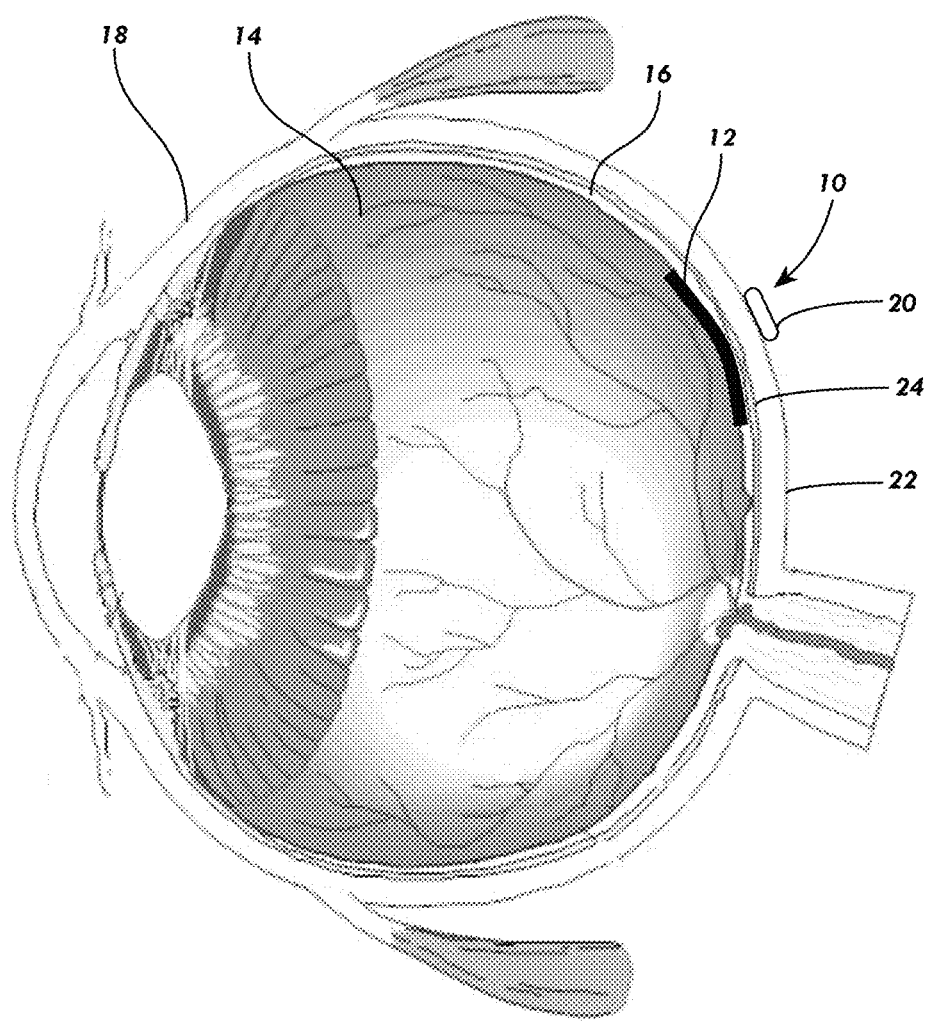
FIG. 1 is an illustration of a magnetic retinal treatment apparatus according to one embodiment of the disclosure.

FIG. 1 shows a basic embodiment of a retinal detachment apparatus 10 of the present disclosure. The retinal treatment apparatus 10 of the present disclosure includes a patch 12 positioned within an interior cavity 14 of an eye 18 and secured adjacent to a retina 16 of the eye 18. A permanent magnet 20 is positioned adjacent to an outer surface 22 of the eye 18 and pulls the patch 12 towards the retina 16, thereby maintaining the retina 16 against an underlying support tissue 24 of the retina 16.

The patch 12 is preferably formed of a medical grade silicone elastomer, such as, for example, Dow Corning® QP1 silicone elastomer, Dow Corning Silastic® silicone elastomer or other biocompatible elastomeric material for implanting in the eye. The patch 12 is flexible to a degree wherein the patch 12 can be manipulated to conform to a shape substantially the same as the applicable retina 16 when the patch is placed adjacent the retina 16. The patch 12 may be formed into one or more shapes based on the particular area of the retina 16 to be treated. For example, in one embodiment the patch 12 may be formed into one or more rectangular shapes. In other embodiments, the patch 12 may be formed into circular, polygonal or other like shapes for being secured adjacent to the retina 16. The size of the patch 12 be selected based on a size of retinal defect to be corrected and a desired location of the patch. For example, in one embodiment the size of the patch 12 may be relatively large, with an area of approximately 800 mm$^2$ such that the patch 12 provides support for a large area of the retina 16. In an alternative embodiment, the patch 12 may be relatively small with an area of approximately 5 mm$^2$ to provide support over a desired portion of the retina 16. Further, the patch 12 preferably has a thickness of from about 0.5 mm to about 2 mm.

An optional low friction coating may be formed on an outer surface of the elastomer patch 12 to reduce any "sticking" or friction between the patch 12 and a surface of the retina 16 when the patch 12 is secured adjacent to the retina 16. Alternatively, a low friction additive may be added to the elastomeric material to reduce sticking of the patch 12.

Figure 2:
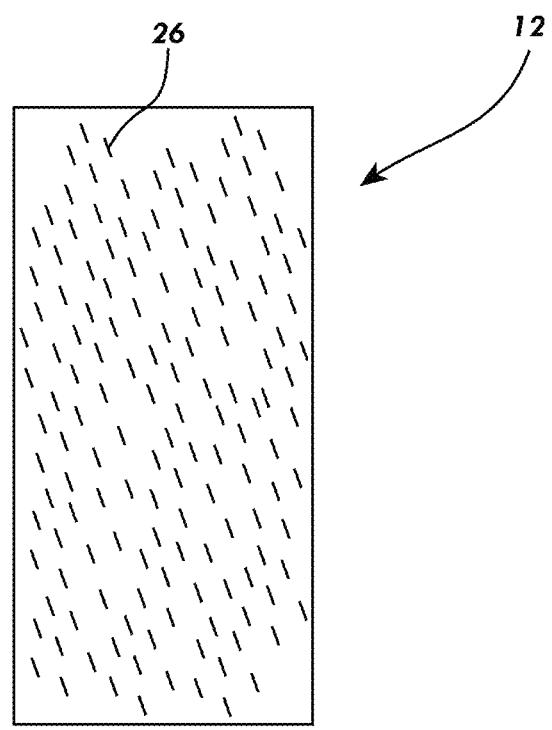
FIG. 2 is an illustration of an elastomeric patch according to one embodiment of the disclosure.

The patch 12 includes a plurality of ferromagnetic particles 26 embedded in the elastomeric material as shown in FIG. 2. The ferromagnetic particles 26 are preferably formed of iron oxide and/or other like magnetic materials. However, it is also understood that the ferromagnetic particles 26 may be formed of other like magnetic particles such as stainless steel filings. In one embodiment, the ferromagnetic particles 26 are preferably evenly spread throughout the patch 12 such that when the magnet 20 is placed adjacent to the patch 12, a substantially equal pressure is applied to the retina 16 over the applicable surface area of the patch 12.

The patch 12 including the embedded ferromagnetic particles 26 is preferably formed by mixing the ferromagnetic particles 26 into a gel or liquid. The ferromagnetic particles 26 may be evenly mixed throughout the gel or liquid before placing the mixture into a mold. The mold may be in the form of a desired shaped of the patch 12, such as a rectangle or other suitable shape. The mixture may then be cured, such as by heat or other known curing techniques, to convert the mixture from a liquid or gel to the elastomeric material of the patch 12. In an alternative embodiment, the mixture of gel or liquid and ferromagnetic particles 26 may be extruded and cured form a substantially continuous patch sheet or roll.

In one embodiment, the patch 12 may be formed by spreading a thin layer of uncured elastomeric material and spreading a plurality of ferromagnetic particles 26 across a surface of the uncured elastomeric material. A following step includes passing a magnetic source adjacent to an underside of the thin layer of elastomeric material, thereby pulling the plurality of ferromagnetic particles 26 into the thin layer of elastomeric material. The thin layer of uncured elastomeric material is then allowed to cure to encapsulate the ferromagnetic particles 26 within the elastomeric material, thereby forming a patch 12 suitable for implantation within an eye.

Referring again to FIG. 1, the permanent magnet 20 is preferably a rare-earth magnet such as, for example, a neodymium magnet. However, other permanent magnets that are capable of producing a strong enough magnetic field to maintain the patch 12 against the retina 16 may be suitable for use. The size of the permanent magnet 20 can vary based on the size of the patch 12 and the amount of force desired to be applied to the retina 16. The permanent magnet 20 may be formed in various shapes such as circular, rectangular, or other like shapes.

Figure 3:
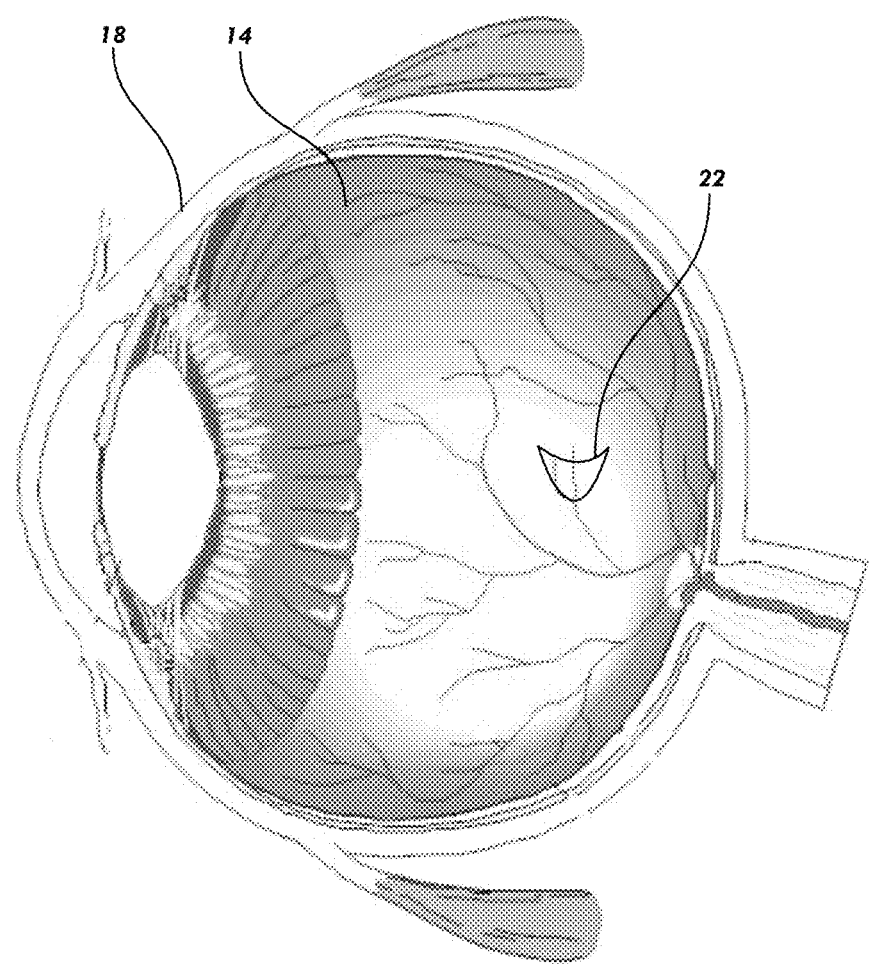
FIG. 3 is an illustration of an eye including a retinal tear according to one embodiment of the disclosure.
Figure 4:
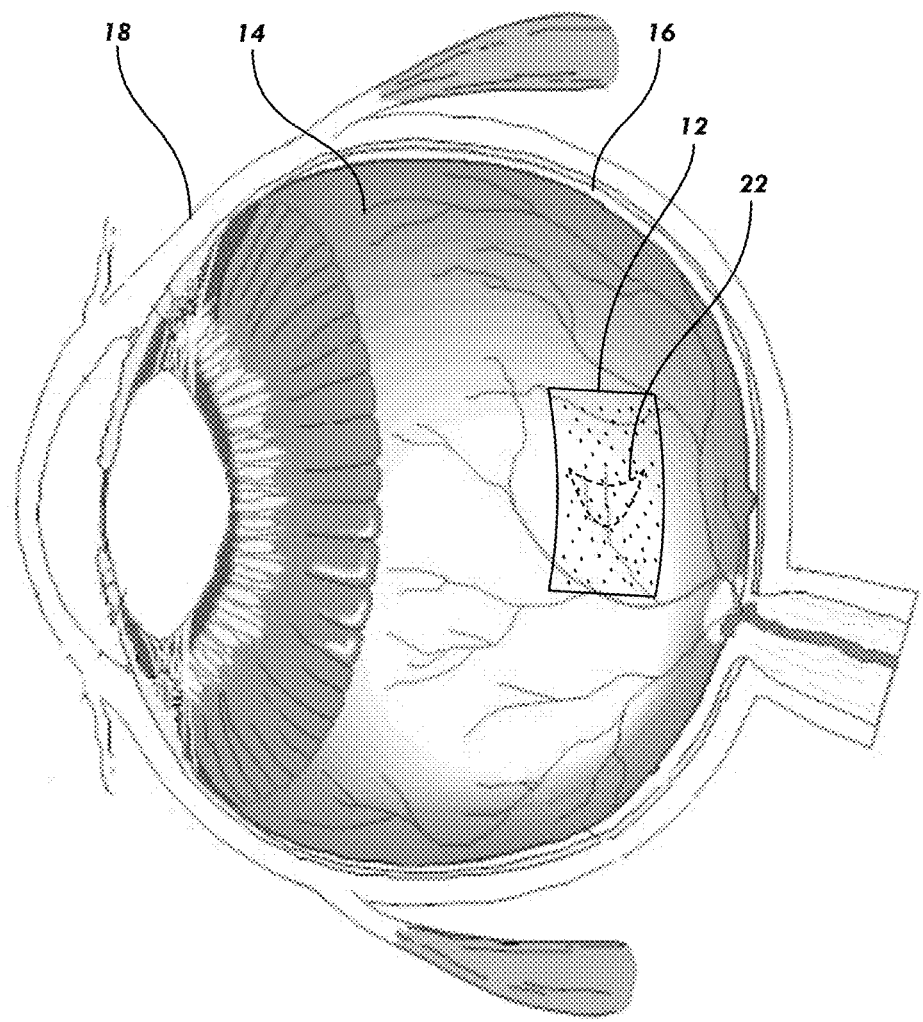
FIG. 4 is an illustration of an elastomeric patch positioned over a retinal tear according to one embodiment of the disclosure.

Referring to FIG. 3, an eye 18 is shown including a hole or tear 28 in the retina 16, such as a hole or tear that occurs during rhegmatogenous retinal detachment. Referring now to FIG. 3, the patch 12 is inserted into the interior cavity 14 through a trocar or separate incision through the sclera of the eye 18 and positioned adjacent the hole or tear 28 in the retina 16. The patch 12 is positioned such that the patch 12 substantially covers the hole or tear 28 in the retina as shown in FIG. 4. The permanent magnet 20 is placed adjacent the exterior of the eye 18 and adjacent the hole or tear 28 in the retina 16. When the permanent magnet 20 is in position adjacent the hole or tear 28, the embedded ferromagnetic particles 26 of the patch 12 are attracted towards the retina 16, thereby pressing the retina 16 towards the underlying support tissue 24 of the eye 18 with the patch 12. The patch 12 is preferably secured adjacent to the retina 16 by capillary action between a surface of the patch 12 and a surface of the retina after positioning the patch 12 with the magnet 20 such that the patch is capable of being secured adjacent to the retina 16 without requiring an adhesive while allowing the patch 12 to be readily removed from adjacent to the retina without imparting any damage to the retina.

In one embodiment, the magnet 20 is secured to the outer surface 22 of the eye 18, such as with an adhesive, sutures, or a band secured on or around the eye to maintain the magnet 20 against the eye 18. The magnet 20 maintains the patch 12 against the retina 16 until the retina 16 has substantially healed and re-attached to the underlying support tissue 24. After the retina 16 is substantially healed, the magnet 20 may be removed from the outer surface 22 of the eye 18. Further, the patch 12 may be removed from the eye 18 without damaging the retina 16 due to the non-adhesive securing of the patch 12 to the retina 16. In one embodiment, a magnetic retrieval tool may be used to aid in retrieving and removing the patch 12 from the eye 18 wherein the retrieval tool pulls the patch 12 away from the retina 16.

Figure 5:
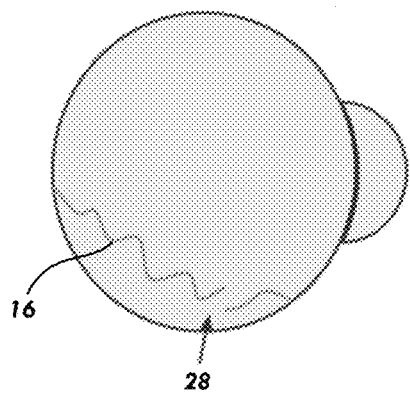
FIGS. 5-9 illustrate the treatment of a retinal tear using a magnetic retinal patch according to one embodiment of the disclosure.
Figure 6:
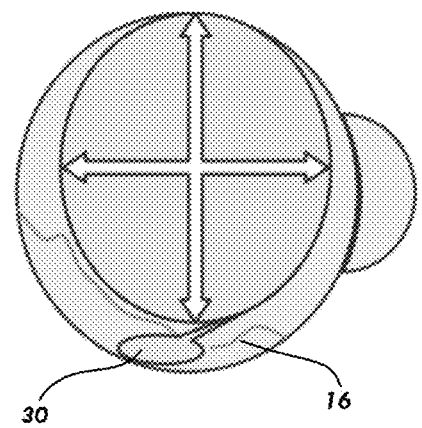

Referring now to FIGS. 5-9, the retinal detachment apparatus 10 may be used in conjunction with a fluid injected into the eye 18 to further maintain the retina 16 in place after installing the patch 12. FIG. 5 shows a retina 16 including the hole or tear 28 as detached from the underlying support tissue 24 of the eye 18. As shown in FIG. 6, simply injecting a fluid 30 into the eye without securing the retina 16 to the underlying support tissue 24 would cause fluid to pass through the hole or tear 28 and into a cavity formed between the retina and underlying support tissue 24 of the eye 18. This would inhibit re-attachment of the retina 16 to the underlying support tissue 24 and may cause further detachment of the retina 16 from the underlying support tissue 24. However, by first supporting the retina 16 against the underlying support tissue 24 of the eye 18 allows a fluid to be injected into the eye to facilitate healing of the retina 16 to the underlying support tissue 24. Suitable fluids and gases include, for example, silicone oil having a viscocity of from about 5,000 centistokes to about 1,000 centistokes, filtered air, sulfur hexafluorane gas, perfluoroprane gas or heavy silicone.

Figure 7:
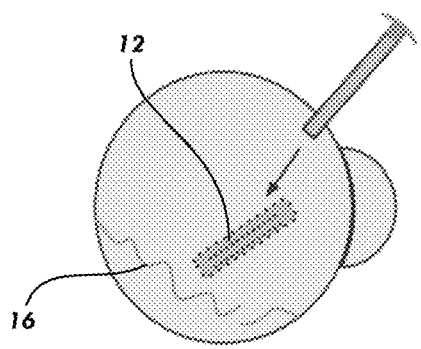
Figure 8:
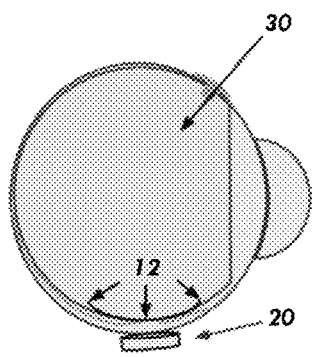
Figure 9:
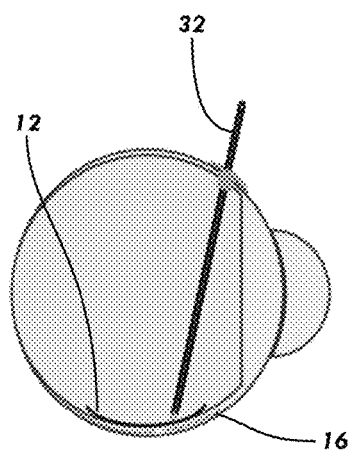

FIG. 7 illustrates inserting the patch 12 of the present disclosure into the eye 18. The patch 12 may be rolled to reduce the size of an incision required to insert the patch 12 into the eye 18. The patch 12 is then unrolled and positioned adjacent to the retina 16 such that the patch 12 substantially covers the hole or tear 28 in the retina 16 as illustrated in FIG. 8. The magnet 20 maintains the patch 12 against the hole or tear 28 of the retina 16. Fluid 30 is then injected into an interior cavity of the eye wherein the patch 12 prevents the fluid from passing through the hole or tear 28 and behind the retina 16. Finally, FIG. 9 illustrates further treating the retina with a concentrated energy beam 32 wherein the patch 12 is substantially transparent, thereby allowing the concentrated energy beam 32 to treat the retina 16 through the patch 12.

Figure 10:
FIG. 10 illustrates a retinal patch formed into an elongate narrow strand according to one embodiment of the disclosure.
Figure 11:
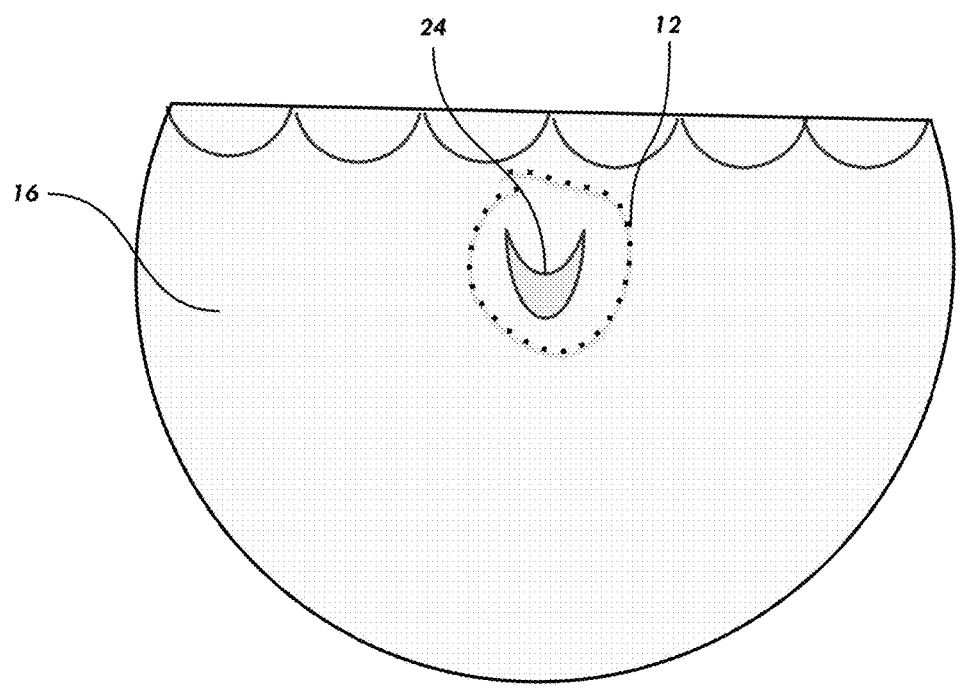
FIG. 11 illustrates forming an elongate narrow retinal patch into a loop on a retina according to one embodiment of the disclosure.

In an alternative embodiment shown in FIG. 10, the patch 12 is formed into an elongate narrow strand. A plurality of the ferromagnetic particles 26 are aligned along a length of the strand within the elongate narrow strand. By forming the patch 12 into an elongate strand, the strand may be positioned adjacent the retina 16 in various configurations to aid in supporting the retina 16. For example, FIG. 11 illustrates forming the elongate strand patch 12 into a loop around a hole or tear 28 in the retina 16 to support the retina 16. In other embodiments, patches 12 formed into one or more strands may be positioned adjacent to the retina 16 in various orientations as required to support the retina 16 while repairing a retinal defect. For example, the one or more strands may be used to pull the retina 16 against underlying tissue 24 by a permanent magnet placed adjacent to the outside of the eye 18 to maintain the retina 16 in place while the retinal defect is repaired. Other configurations of the strand may include, for example, configuring one or more strands of the patches 12 into a rectangular shape around a retinal defect or forming the strands in a crossing pattern over a defect to encourage re-attachment of the retina 16 to the underlying tissue 24.

In one embodiment, the patch 12 may be formed into an elongate continuous roll or continuous sheet. When the patch 12 is to be placed adjacent to a hole or tear in the retina, the patch may be sized and shaped according to a size of the hole or tear in the retina to be repaired. Multiple custom-shaped patches may be formed from the patch comprising a single roll or sheet. The continuous patch roll or sheet may have varying amounts of ferromagnetic particles such that a patch formed from one particular roll or sheet may exert a stronger force on the retina than a patch formed from another particular roll or sheet having fewer ferromagnetic particles within the roll or sheet.

Figure 12:
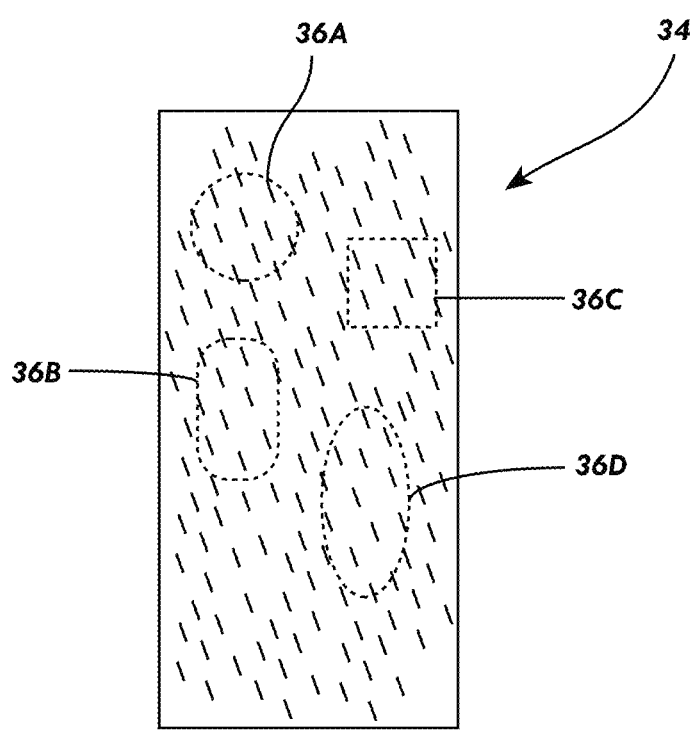
FIG. 12 illustrates a sheet including various pre-cut retinal patches according to one embodiment of the disclosure.

In yet another embodiment, as illustrated in FIG. 12, a sheet 34 may be provided including various pre-cut patches 36 (36A, 36B, 36C, and 36D). When a healthcare professional requires one or more patches 36 for use during a retinal detachment procedure, the healthcare professional may select one or more of the pre-cut patches 36 based on a retinal defect to be cured. Various pre-cut patches 36 may be provided, each having a different size, shape, and/or relative concentration of ferromagnetic particles therein such that the healthcare provider has several options when choosing a particular patch 36 for use during a particular procedure.

Figure 13:
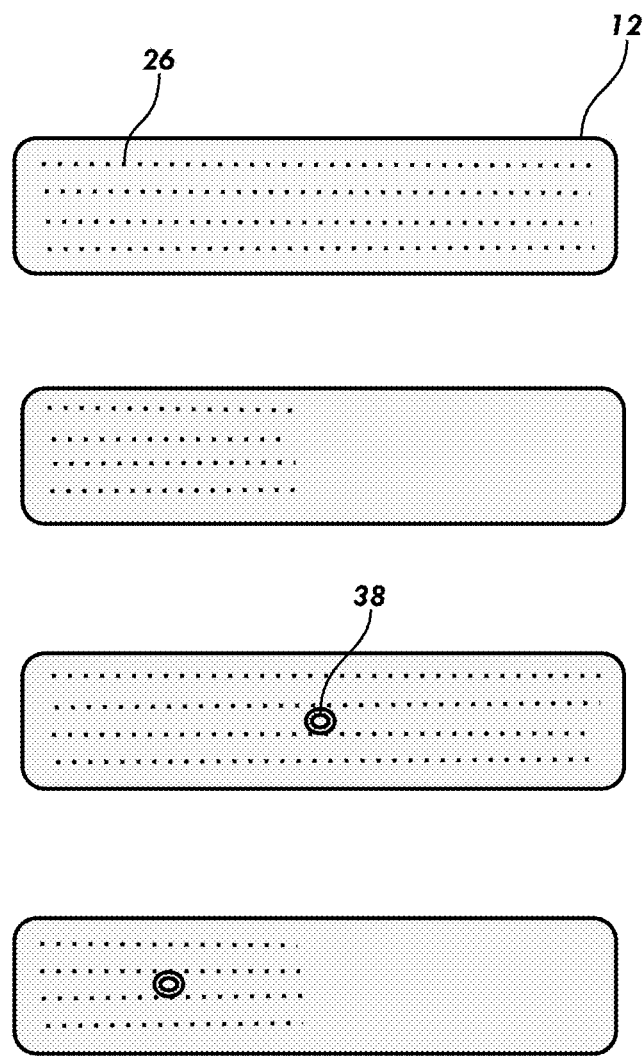
FIG. 13 illustrates alternative distributions of ferromagnetic particles throughout a retinal patch according to one embodiment of the disclosure.

Referring to FIG. 13, while preferably the ferromagnetic particles 26 are uniformly spread throughout the patch, in another embodiment, the ferromagnetic particles 26 may be concentrated in one or more desired areas of the patch 12 such that a greater force is applied over an area where the ferromagnetic particles 26 have greater concentration relative to areas of lesser concentration of ferromagnetic particles 26.

In one embodiment, the patch 12 may include one or more endodrainage sites 38 formed through the patch. The one or more endodrainage sites 38 allow any fluid trapped behind the retina to pass out of the retina, through the endodrainage site 38 and into the interior of the eye.

The retinal detachment apparatus 10 of the present disclosure advantageously provides a removable elastomeric patch for repairing a retina. The plurality of ferromagnetic particles are embedded and substantially contained within the elastomeric patch. The elastomeric patch is inserted into the eye and positioned adjacent to the retina. The magnet located outside of the eye pulls the patch 12 into position adjacent to a retinal detachment to facilitate repair of the retinal detachment. The patch is configured to be removably secured to the retina using the magnet while allowing the patch to be readily removed from the retina after the retina has sufficiently healed so that the patch is no longer required to facilitate re-attachment of the retina to the underlying support tissue. Because the ferromagnetic particles are embedded within the patch, when the patch is removed, all ferromagnetic particles are also removed, thereby ensuring that no ferromagnetic particles remain in the eye. Further, removal of the patch results in immediate removal of the ferromagnetic particles without the need to wait for the particles to be absorbed or otherwise removed from the eye.

It has been found that by forming the patch 12 in accordance with the disclosure above, the patch 12 is substantially capable of being secured to the retina without the use of an adhesive, thereby allowing the patch to be readily removed from the retina without damaging the retina when the retina is substantially healed. When the patch 12 is removed from the eye, the ferromagnetic particles within the patch are removed from the eye as well such that individual magnetic particles do not have to be retrieved from the interior of the eye. Further, the patient is not required to wait until any ferromagnetic particles within the eye are substantially absorbed by the eye and surrounding tissue before receiving an MRI or other magnetic treatment.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A retinal treatment apparatus for treatment of a detached retina of an eye, the treatment apparatus comprising:

an elastomeric patch formed of a biocompatible and non-adhesive material, the elastomeric patch configured to be inserted into the eye through an incision in a sclera of the eye and positioned adjacent the detached retina and subsequently removed from the eye after a treatment period;

a plurality of ferromagnetic particles encapsulated within the elastomeric patch wherein when the elastomeric patch is removed from the eye the plurality of encapsulated ferromagnetic particles is also removed; and a permanent rare-earth magnet adapted to be secured adjacent to an exterior surface of the eye adjacent to the removable elastomeric patch to compel the elastomeric patch against the retina such that the permanent rare-earth magnet is aligned with a detached portion of the retina.

2. The retinal treatment apparatus of claim 1, wherein the elastomeric patch comprises a silicone elastomer.

3. The retinal apparatus of claim 2, wherein the silicone elastomer consists essentially of commercially available Silastic®.

4. The retinal treatment apparatus of claim 1, wherein the ferromagnetic particles comprise iron oxide.

5. The retinal treatment apparatus of claim 1, wherein the elastomeric patch has a thickness ranging from about 0.5 mm to about 2 mm.

6. The retinal treatment apparatus of claim 1, wherein the elastomeric patch comprises a treatment area of from about 5 mm$^2$ to about 800 mm$^2$.

7. The retinal treatment apparatus of claim 1, wherein the elastomeric patch is formed into an elongate narrow strand and wherein the ferromagnetic particles are positioned along a length of the elongate strand, wherein the elongate narrow strand is configured to be shaped around a detached area of a retina.

8. The retinal treatment apparatus of claim 1, wherein the ferromagnetic particles are substantially evenly distributed throughout the elastomeric patch.

9. The retinal treatment apparatus of claim 1, wherein the ferromagnetic particles are non-uniformly distributed throughout the patch such that the ferromagnetic particles are concentrated in one or more spaces within the elastomeric patch, wherein the one or more spaces are located along the patch where greater force is desired to be applied by the patch.

10. The retinal treatment apparatus of claim 1, further comprising an adhesive for securing the permanent rare-earth magnet to the exterior surface of the eye.

11. The retinal treatment apparatus of claim 1, further comprising a band positioned around and adjacent to an exterior of the eye for temporarily holding the permanent rare-earth magnet against the exterior surface of the eye.

12. The retinal treatment apparatus of claim 1, wherein the patch is substantially transparent.

13. The retina treatment apparatus of claim 1, wherein the elastomeric patch further includes a low friction additive configured to ease removal of the elastomeric patch from the eye after the treatment period.

14. A retinal treatment apparatus for treatment of a detached retina of an eye, the treatment apparatus comprising:

an elastomeric patch formed of a biocompatible and non-adhesive material comprising a silicone elastomer, the elastomeric patch configured to be inserted into the eye through an incision in a sclera of the eye and positioned adjacent the detached retina and subsequently removed from the eye after a treatment period;

a plurality of ferromagnetic particles encapsulated within the elastomeric patch wherein when the elastomeric patch is removed from the eye the plurality of encapsulated ferromagnetic particles are also removed; and a permanent rare-earth magnet adapted to be secured adjacent to an exterior surface of the eye adjacent to the removable elastomeric patch to compel the elastomeric patch against the retina such that the permanent rare-earth magnet is aligned with a detached portion of the retina; and a band positioned around and adjacent to an exterior of the eye for temporarily holding the permanent rare-earth magnet against the exterior surface of the eye.

* * * * *